United States Patent [19]

Brenner et al.

[11] Patent Number: 5,049,140

[45] Date of Patent: Sep. 17, 1991

[54] ANTIMICROBIAL FITTING FOR MEDICAL CATHETERS AND METHOD FOR THEIR APPLICATION

[75] Inventors: Otto Brenner, Edingen; Christoph Josefiak, Rimbach; Günter Schuhmacher, Weinheim, all of Fed. Rep. of Germany

[73] Assignee: Firma Carl Freudenberg, Weinheim/Bergstrasse, Fed. Rep. of Germany

[21] Appl. No.: 467,951

[22] Filed: Jan. 22, 1990

[30] Foreign Application Priority Data

May 22, 1989 [DE] Fed. Rep. of Germany ....... 3916648

[51] Int. Cl.⁵ .................... A61M 25/00; A61M 5/32
[52] U.S. Cl. ................... 604/266; 604/265; 604/280; 604/282; 604/283
[58] Field of Search ............... 604/264, 265, 266, 267, 604/280, 282, 283

[56] References Cited

U.S. PATENT DOCUMENTS

| 4,603,152 | 7/1986 | Laurin et al. | 604/265 |
| 4,677,143 | 6/1987 | Laurin et al. | 604/265 |
| 4,886,505 | 12/1989 | Haynes et al. | 604/265 |
| 4,973,320 | 11/1990 | Brenner et al. | 604/265 |

FOREIGN PATENT DOCUMENTS 0098688 1/1984 European Pat. Off.

Primary Examiner—Robert Bahr
Assistant Examiner—Lynne A. Reichard
Attorney, Agent, or Firm—Kenyon & Kenyon

[57] ABSTRACT

A tube or ring-shaped, elastic cuff is used as a antimicrobial fitting for medical catheters. The fitting is manufactured from organic silicon/polyurethane elastomer including an antimicrobial agent. The fitting is annularly disposed on a catheter and held in place by radial tension. The fitting has very high tensile strength and resistance to tearing and preferably has a wall thickness of about 0.1 mm; may be cut into segments of 2 to 10 cm long; and can be drawn onto a catheter as individual segments.

9 Claims, 1 Drawing Sheet

ANTIMICROBIAL FITTING FOR MEDICAL CATHETERS AND METHOD FOR THEIR APPLICATION

FIELD OF THE INVENTION

The subject invention relates to a fitting or cuff having antimicrobial properties useful in reducing the inflammations and infections associated with medical catheters especially urethral catheters and a method for attaching the fitting to a catheter.

BACKGROUND OF THE INVENTION

Medical catheters, particularly uretheral catheters, which incorporate antimicrobial agents that release metallic ions when introduced to a body cavity for reducing inflammation and infection, are usually made in either of two methods. In the first method, the catheter surfaces are treated with a lacquer which includes an antimicrobial agent as described in U.S. Pat. Nos. 4,054,139 and 4,612,337. This method has the disadvantage of involving multiple steps, such as, soaking, saturating and drying the catheter material.

In the second method, the entire catheter is manufactured with a solid polymer material which contains an antimicrobial agent. This method has the disadvantages of being expensive and involving a complicated manufacturing process because catheters require various types of surface geometry that may be difficult to achieve with polymers that have been modified with antimicrobial agents. Moreover, this method is substantially more expensive because it requires larger amounts of antimicrobial agents than the above-described coating method.

The term antimicrobial as used herein means a material or substance capable of destroying or suppressing the growth microorganisms that cause inflammations and infection in and around body cavities.

OBJECTS AND SUMMARY OF THE INVENTION

An advantage afforded medical catheter manufacturers by the present invention is that they can fabricate their products without being constrained by limitations on choice of materials or processes that are required to provide the antimicrobial properties necessary to avoid inflammation and infection.

It is an object of this invention to provide a fitting for catheters that can be easily and inexpensively manufactured and that provides the antimicrobial activity required in medical catheter applications.

It is another object of this invention to provide a fitting for catheters that has effective and long lasting antimicrobial properties.

It is yet another object of this invention to provide an antimicrobial fitting that can be securely attached to catheters of various sizes and shapes especially conventional uretheral catheters, and to provide a method for attaching the fittings to such catheters.

It is still another object of this invention to provide a tear resistant, tubular antimicrobial fitting for catheters that has a surface roughness of less than about 6 micrometers to ease insertion into a body cavity and prevent injury.

The present invention provides an antimicrobial fitting for a catheter comprising an elastic tubular member having a Shore-A hardness (DIN 53 305) of about 80 to 95 and which is fabricated from a silicone/polyurethane elastomer comprised of less than about 50% wt. of an organic silicone polymer having a molecular weight of about 500 to 10,000 and about 1 to 15% wt. of an antimicrobial agent based on the weight of the elastomer.

The present invention also provides a method for making a catheter having antimicrobial properties, comprising the steps of preparing a fitting comprised of a tubular member fabricated with an organic silicon/polyurethane elastomer including less than about 50% wt. organic silicone polymer having a molecular weight of about 500 to 10,000 and having an antimicrobial agent uniformly dispersed therein; sizing the tubular member so that its inside diameter is less than or equal to the outside diameter of the catheter; cutting said tubular member into segments and drawing a plurality of the segments onto the catheter.

The invention also provides a catheter having the above-described fitting annularly disposed thereon. The fitting's tubular member is preferably cut into segments of about 2 to 10 cm preferably 5 cm in length which are spaced along the catheter's elongate flexible member at about 0.1 to 3.0 cm preferably 0.2 to 0.4 cm.

DETAILED DESCRIPTION OF THE INVENTION

Figure 1:
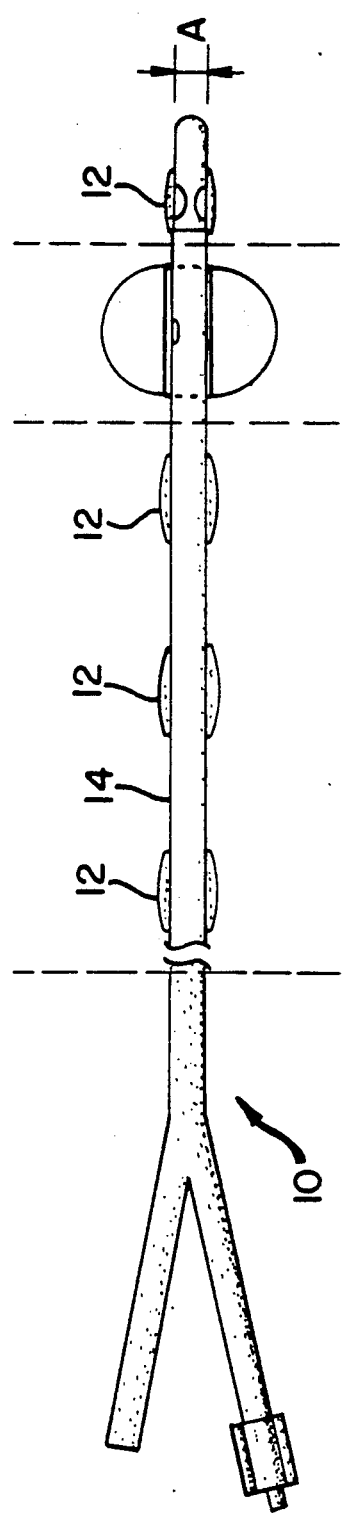
FIG. 1 illustrates a catheter having a plurality of fittings made and installed in accordance with the invention.

FIG. 1 depicts a conventional catheter 10 having fittings 12, according to the invention, slid onto or over the catheter shaft 14 as a cuff or sleeve. The fittings 12 comprise a very thin elastomeric plastic tube having an antimicrobial agent embedded in it. The antimicrobial agent may be a metal, metallic salt or other compound containing metallic ions, an oxide, carbide or sulphate or an organic metallic compound which give off or release metallic ions for example, $Ag^+$, $Au^+$ or $Cu^{++}$ in an amount effective to destroy or suppress the growth of microorganisms. Silver sulphate is a preferred antimicrobial agent.

A useful elastomer is polyurethane, preferably a polyester polyurethane, modified with an organic silicone. Applicants' copending Patent Applications F.R. Germany P 37 25 728 and corresponding U.S. Ser. No. 227,374 now U.S. Pat. No. 4,973,320 issued 23 Mar. filed Aug. 13, 1988, the text of which is incorporated herein by reference describe the preparation of such elastomers. The elastomer contains in its main chain less than about 50% wt. of an organic silicone polymer having a molecular weight of about 500 to 10,000. The elastomer further includes 1 to 15% wt. antimicrobial agent, based on the total weight of the elastomer. The antimicrobial agent is uniformly dispersed in the elastomer.

According to the invention, fittings 12 suitable for attachment to catheters are easily manufactured from the elastomer by known tube extrusion techniques. Preferably, the fittings 12 have a tensile resistance of about 20 MPa and a breaking elongation of about 500%, exhibit a Shore-A hardness between about 80 and 95 and have a surface roughness under about 6 micrometers.

Conventional urethral catheters found on the market today are available in three classes of thickness:

1. 26 to 19 Charrière units (=8.7 to 6.3 mm outside diameter);
2. 18 to 13 Charrière units (=6.0 to 4.3 mm outside diameter);
3. 12 to 8 Charrière units (=4.0 to 2.7 mm outside diameter).

The fittings of this invention can be provided in three different interior diameters suitable for attachment to the variously sized catheters in each of the three Charrière classes. Preferably the interior diameter (B) of the fitting will be selected so that it is somewhat smaller than the exterior diameter (A) of the catheter it is to be drawn onto. Preferably, the fitting interior diameter (B) will be in proportion to the exterior diameter (A) of the catheter in a ratio of about 1 : 1.2 to 1 : 1.8. The fittings of the invention suitable for uretheral catheters are therefore manufactured so that their interior diameter lies between about 1.5 and 7.5 mm in order to be able to be drawn onto catheters in each of the three Charrière classes without radial stress damage.

The stretching of the fitting around the catheter causes it to be securely attached. Experience has shown that despite the stretching forces, no damage to the fitting occurs during drawing of an appropriately sized fitting onto a catheter or during its use.

The thickness of the fitting wall 16 should be selected to avoid disadvantageously lowering the flexibility needed to draw the catheter through the fitting. Wall thicknesses of about 0.1 mm with a tolerance limit of about ± 5% are preferred.

After extrusion of the elastomer, the resultant tubular member may be cut into 2 to 10 cm long segments or bands that comprise fitting 12, which may then be refused at a temperature between about 180° and 220° C. in order to effect a rounding 18 of the cut edges at the fitting ends. This measure lessens the chances of injury from sharp junctions between the fitting and catheter when the catheter is inserted into a body cavity.

In one especially economical embodiment the fitting comprises a plurality of individual segments of about 5 cm each which are individually drawn onto a catheter. The segments are axially spaced from each other by about 0.1 to 3.0 cm and a spacing of 0.2 to 0.4 cm is preferred for additional safety. In addition to saving materials, this embodiment has the advantage of providing greater catheter flexibility without loss of antimicrobial effectiveness. The formation of an "inhibiting zone" for microbial, e.g., bacterial growth, by the metallic ions from neighboring segments effectively covers the uncovered surfaces of the length of the catheter.

Figure 3:
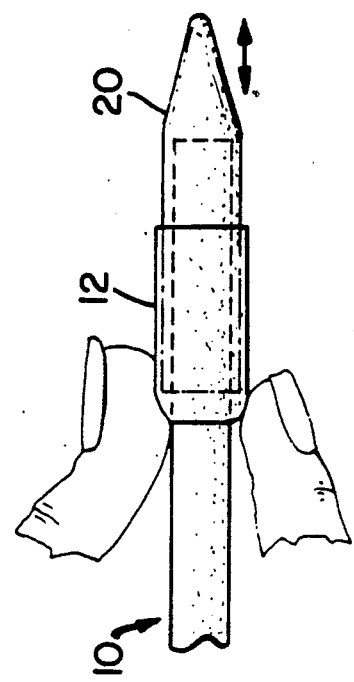
FIG. 3 illustrates manual installation of the fittings of the invention with a cone-shaped guide.
Figure 2:
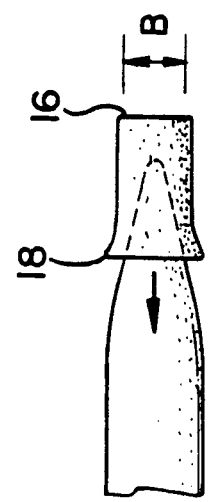
FIG. 2 illustrates a Teflon ® cone-shaped guide used to install the fittings of the invention.

When drawing the fitting 12 onto a catheter shaft 14, a cone-shaped guide 20, a shown in FIGS. 2 and 3, can be used. Preferably, the cone-shaped guide 20 is made of polytetrafluoroethylene (PTFE) and has a largest diameter that is greater than the exterior diameter (A) of the catheter shaft 20 it will be used within and a smallest diameter about half as large as the largest diameter. A single cone-shaped guide 20 may be used within the entire range of catheter sizes in Charrière class.

In practical terms the length of the guide 20 will be about 40 to 50 cm. A fitting 12 is drawn over the guide's tapered end and thereby stretched to approximately 80% of its thinnest expanse. The guide 20 is then positioned with its largest diameter end to a catheter shaft 14, so that the fitting 12 can be stripped from the guide in the direction of and onto the catheter as shown in FIG. 3. The cone-shaped guide 20 ensures that the fitting 12 is stretched evenly along its entire expanse while being drawn onto a catheter shaft 14 and thus smooth operation is assured.

The following Table illustrates the mechanical requirements and sizes of three fittings made in accordance with the invention each of which can be drawn under an initial stress onto a catheter within the corresponding Charrière class.

| Charrière Class Catheter Units | Interior Diameter of the Fitting, mm | Fitting Maximum | Elongation Minimum |
| --- | --- | --- | --- |
| 26 to 19 | 5.8 | 50% | 9% |
| 18 to 13 | 4.0 | 50% | 8% |
| 12 to 8 | 2.5 | 60% | 8% |

It can be seen from the data presented in the Table that the fittings of the invention need not be stretched beyond their elastic limit during installation on a catheter.

What is claimed is:

1. An antimicrobial fitting for a catheter, comprising:
   a tubular member having a Shore A hardness between about 80 and 95 fabricated from a silicone/polyurethane elastomer comprised of less than about 50% wt. organic silicone polymer having a molecular weight of about 500 to 10,000, and about 1 to 15% wt. of an antimicrobial agent uniformly dispersed in said elastomer and wherein the tubular member has a tensible strength of about 20 MPa, a breaking elongation of about 500% and a surface roughness less than about 6 micrometers.

2. The fitting of claim 1, wherein:
   the antimicrobial agent is selected from the group consisting of metals, metal salts, oxides, carbides and sulphates and organometalic compounds, that release metal ions from the silicone/polyurethane elastomer in antimicrobially effective amounts.

3. The fitting of claim 1, wherein:
   the fitting is for a uretheral catheter and the tubular member has a wall thickness of about 0.1 micrometer, and interior diameter of about 1.5 to 7.5 mm.

4. The fitting of claim 3, wherein:
   the antimicrobial agent is silver sulfate.

5. The fitting of claim 1, wherein:
   said tubular member comprises a plurality of segments.

6. The fitting of claim 3, wherein:
   said tubular member comprises a plurality of segments of about 2 to 10 cm in length.

7. A method for making a catheter having antimicrobial properties, comprising the steps of:
   preparing a fitting comprising a tubular member fabricated with an organic silicone/polyurethane elastomer including less than about 50% wt organic silicone polymer having a molecular weight of about 500 to 10,000 and having an antimicrobial agent uniformly dispersed therein;
   sizing said tubular member so that it has an inside diameter that is about equal to or less than the catheter's outside diameter;
   cutting said tubular member into segments; and drawing a plurality of said segments onto a portion of the catheter which will be inserted into a body cavity.

8. The method of claim 7 wherein the inside diameter of said tubular member and the outside diameter of said catheter are in a ratio of about 1:1.2 to 1:1.8; said segments are about 5 cm long and are spaced abut 1 to 3 cm apart on said catheter.

9. The method of claim 8 wherein the segments cover at least about 50% of an exposed surface of the catheter portion.

* * * * *

UNITED STATES PATENT AND TRADEMARK OFFICE
CERTIFICATE OF CORRECTION

PATENT NO.   :   5 049 140

DATED        :   September 17, 1991

INVENTOR(S)  :   Otto BRENNER et al.

It is certified that error appears in the above-identified patent and that said Letters Patent is hereby corrected as shown below:

```
Column 2, lines 52,53: change "... issued.....1988..."
to read --...227,374, filed Aug. 2, 1988, now
US Pat. No. 4,973,320 issued Nov. 27, 1990...--.
```

Signed and Sealed this

Thirteenth Day of April, 1993

*Attest:*

STEPHEN G. KUNIN

*Attesting Officer*     *Acting Commissioner of Patents and Trademarks*